(12) United States Patent
Lee (10) Patent No.: US 12,016,742 B2
(45) Date of Patent: Jun. 25, 2024

(54) TOOTH WHITENING DEVICE

(71) Applicant: Soon Ho Lee, Seoul (KR)

(72) Inventor: Soon Ho Lee, Seoul (KR)

(73) Assignee: Soon Ho Lee, Seoul (KR)

( * ) Notice: Subject to any disclaimer, the term of this patent is extended or adjusted under 35 U.S.C. 154(b) by 82 days.

(21) Appl. No.: 16/625,380

(22) PCT Filed: Nov. 16, 2017

(86) PCT No.: PCT/KR2017/012986
§ 371 (c)(1),
(2) Date: Dec. 20, 2019

(87) PCT Pub. No.: WO2018/236004
PCT Pub. Date: Dec. 27, 2018

(65) Prior Publication Data
US 2021/0008384 A1    Jan. 14, 2021

(30) Foreign Application Priority Data

Jun. 22, 2017 (KR) .......................... 10-2017-0079222

(51) Int. Cl.
*A61C 17/06* (2006.01)
*A61C 19/06* (2006.01)
*A61N 5/06* (2006.01)

(52) U.S. Cl.
CPC ............ *A61C 17/06* (2019.05); *A61C 19/066* (2013.01); *A61N 5/0603* (2013.01); *A61N 5/062* (2013.01);
(Continued)

(58) Field of Classification Search
CPC ............ A61C 17/06; A61C 19/06–066; A61N 2005/0606; A61N 5/062
See application file for complete search history.

(56) References Cited

U.S. PATENT DOCUMENTS 6,893,259 B1 *  5/2005  Reizenson ......... A61C 17/0211
                                                           433/29
2005/0244792 A1 * 11/2005  Verdi ................... A61C 19/066
                                                           433/215
(Continued)

FOREIGN PATENT DOCUMENTS

FR           3000381 A1 *  7/2014  ........... A61C 19/066
JP           2015512761        4/2015
(Continued)

OTHER PUBLICATIONS

International Search Report—PCT/KR2017/012986 dated Mar. 22, 2018.

*Primary Examiner* — Jacqueline T Johanas
*Assistant Examiner* — Shannel Nicole Belk
(74) *Attorney, Agent, or Firm* — Revolution IP, PLLC (57) ABSTRACT

Provided is a tooth whitening device capable of performing tooth whitening treatment. The tooth whitening device can be disposable. The tooth whitening device comprises: a main frame provided in a horseshoe shape and having a whitening groove in which teeth can be fitted; a support member coupled to the main frame; a plurality of light-emitting members installed inside the main frame and configured to emit light during tooth whitening; a fluid storage member positioned to extend through the insides of the main frame and the support member, and configured to store a fluid such as saliva flowing out of the mouth during the tooth whitening; and a control member for controlling a light-emitting time or operation of the light-emitting member, wherein the whitening groove is coated with a gel-type whitener.

5 Claims, 6 Drawing Sheets (52) U.S. Cl.
CPC .......... *A61N 2005/0606* (2013.01); *A61N 2005/0626* (2013.01); *A61N 2005/0654* (2013.01)

(56) References Cited

U.S. PATENT DOCUMENTS

| | | | | |
|---|---|---|---|---|
| 2012/0021375 A1* | 1/2012 | Binner | ............... | A61C 17/065 433/89 |
| 2015/0044628 A1* | 2/2015 | Flyash | ............... | A61C 17/16 433/27 |
| 2018/0263746 A1* | 9/2018 | Demarest | ............ | A61C 19/066 |

FOREIGN PATENT DOCUMENTS

| | | | | |
|---|---|---|---|---|
| KR | 100773379 | 11/2007 | | |
| KR | 20100000287 | 1/2010 | | |
| KR | 101365381 | 2/2014 | | |
| KR | 101527727 | 6/2015 | | |
| WO | WO-2015083155 A1 * | 6/2015 | ........... | H05H 1/2406 |

\* cited by examiner

TOOTH WHITENING DEVICE

TECHNICAL FIELD

The present invention relates to a tooth whitening device, and more particularly, to a tooth whitening device capable of easily performing tooth whitening treatment in ordinary environments.

BACKGROUND ART

Recently, many people are interested in well-being. People have come to enjoy material affluence due to industrialization and thus people are paying more attention to how to enjoy a better life than what they will eat to survive.

People make an effort to change their appearances beautifully as a method of keeping their lives more beautiful. As an example among them, there is a tooth whitening method of whitening their teeth. Tooth whitening may give an impression of a clean appearance to people they meet. In an early state of tooth whitening, as one of the simplest methods, a whitening effect is obtained by brushing the teeth using toothpaste including a small amount of a tooth whitening agent.

However, since the amount of the tooth whitening agent included in the toothpaste is too small, it is impossible to effectively remove coloring matter pigmented on a tooth surface.

In order to perform more effective tooth whitening treatment, a method of performing specialized treatment such as using high levels of a tooth whitening agent, tooth whitening treatment accompanying light emission, and the like has been used in a dental clinic. However, although this method provides an excellent tooth whitening effect, there are problems such as the inconvenience of visiting a dental clinic to receive treatment and high medical expenses being required.

DISCLOSURE

Technical Problem

The present invention is directed to providing a tooth whitening device which allows tooth whitening treatment to be easily performed in ordinary environments and which is disposable.

The present invention is also directed to providing a tooth whitening device allows a tooth whitening agent to be prevented from being diluted by being mixed with saliva or prevents saliva from flowing outward during tooth whitening treatment.

Technical Solution

One aspect of the present invention provides a disposable tooth whitening device. The tooth whitening device includes a main frame provided in a horseshoe shape and including tooth whitening grooves capable of holding teeth, a support member coupled to the main frame, a plurality of light emitting members installed in the main frame and configured to emit light during tooth whitening, a fluid storage member located to pass through the main frame and an inside of the support member, and configured to store saliva and the like flowing from an inside of a mouth during the tooth whitening, and a control member configured to control a light emission time of the light emitting members and whether the light emitting members operate. Here, a gel type tooth whitening agent is applied to the tooth whitening grooves.

The main frame may include an inner frame provided in a horseshoe shape, an outer frame provided in a horseshoe shape and located to be spaced apart from the inner frame, and a bottom frame coupled with the inner frame and the outer frame and located between the inner frame and the outer frame.

The tooth whitening grooves may be provided to be surrounded by the inner frame, the outer frame, and the bottom frame.

The inner frame, the outer frame, and the bottom frame may be formed of a transparent plastic material.

The light emitting members may include a plurality of lamps, and the plurality of lamps may be spaced at certain intervals apart from an inner wall of the main frame surrounding the tooth whitening grooves.

The fluid storage member may include a fluid inlet formed on a surface of the main frame opposite to a part coupled with the support member, a fluid outlet formed on one side surface of the support member, a fluid channel located inside the main frame and the support member and having one end connected to the fluid inlet and the other end connected to the fluid outlet to move a fluid flowing through the fluid inlet toward the fluid outlet, and a fluid storage portion coupled with the support member and configured to store the fluid discharged from the fluid outlet.

The fluid storage portion may be detachably coupled with the support member.

The control member may include a manipulation portion configured to control whether the light emitting members emit light and a timer portion configured to control a light emission time of the light emitting members.

The manipulation portion may include a manipulation lamp configured to continuously emit light outward while the light emitting members emit light.

Advantageous Effects

According to one embodiment of the present invention, a tooth whitening device provides an advantage of easily performing tooth whitening treatment in ordinary environments such as home, office, and the like.

According to one embodiment of the present invention, since it is possible to prevent a fluid such as saliva and the like in the mouth from being mixed with a tooth whitening agent or from flowing outward from a mouth during tooth whitening treatment and to store the tooth whitening agent in a fluid storage portion, tooth whitening treatment may be easily performed.

Also, since a power supply portion is included in a manipulation portion, tooth whitening treatment may be easily performed without the inconvenience of additionally connecting a power supply or inserting a battery.

Also, a tooth whitening device according to the present invention may be disposable and may be sanitarily and simply used.

DESCRIPTION OF DRAWINGS

The following drawings attached to the specification illustrate one embodiment of the present invention and further enlighten the technical concept of the present invention with the following description. However, the present invention should not be construed to be limited to items shown in the drawings.

MODES OF THE INVENTION

Hereinafter, embodiments of the present invention will be described in detail with reference to the attached drawings. The embodiments of the present invention may be modified in a variety of forms, and the scope of the present invention should not be construed as being limited to the following embodiments. The embodiments are provided to completely describe the present invention to one of ordinary skill in the art. Accordingly, throughout the drawings, shapes of elements may be exaggerated for more distinct description. Also, the terms used in the specification and the claims should not be limited to general or lexical meanings and should be interpreted as meanings and concepts coinciding with the technical concept of the present invention on the basis of a principle in which the inventor can appropriately define the concept of the terms to describe the invention in the best manner.

The present invention provides a tooth whitening device. The tooth whitening device according to the present invention may allow a user to autonomously perform tooth whitening treatment using the tooth whitening device. The tooth whitening device according to the present invention may be disposable.

Figure 1:
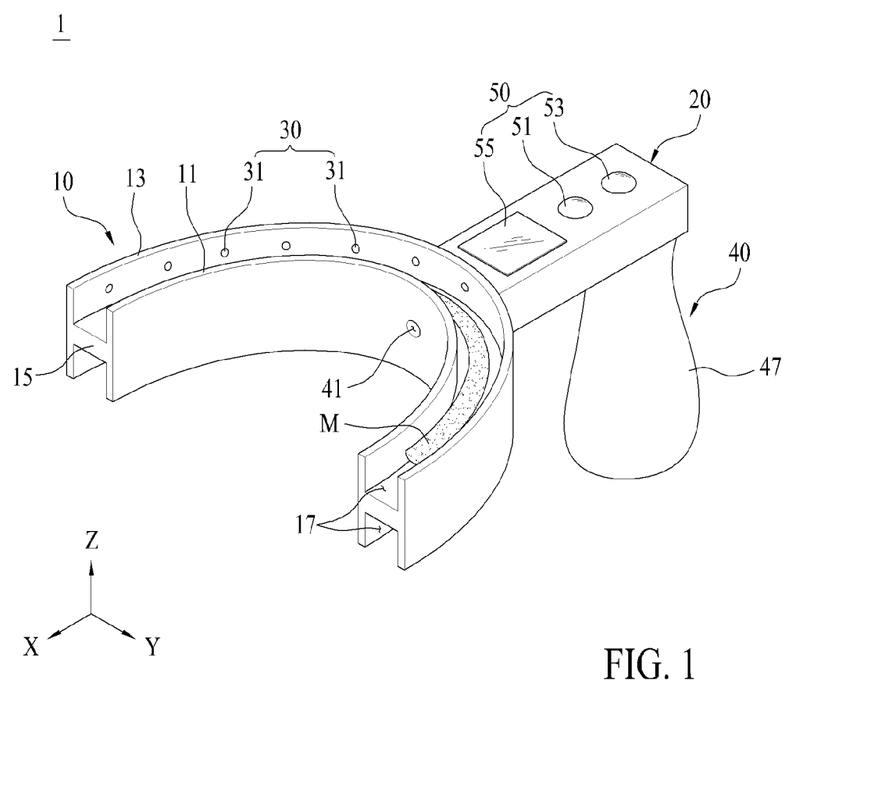
FIG. 1 is a perspective view illustrating a tooth whitening device according to one embodiment of the present invention.
Figure 2:
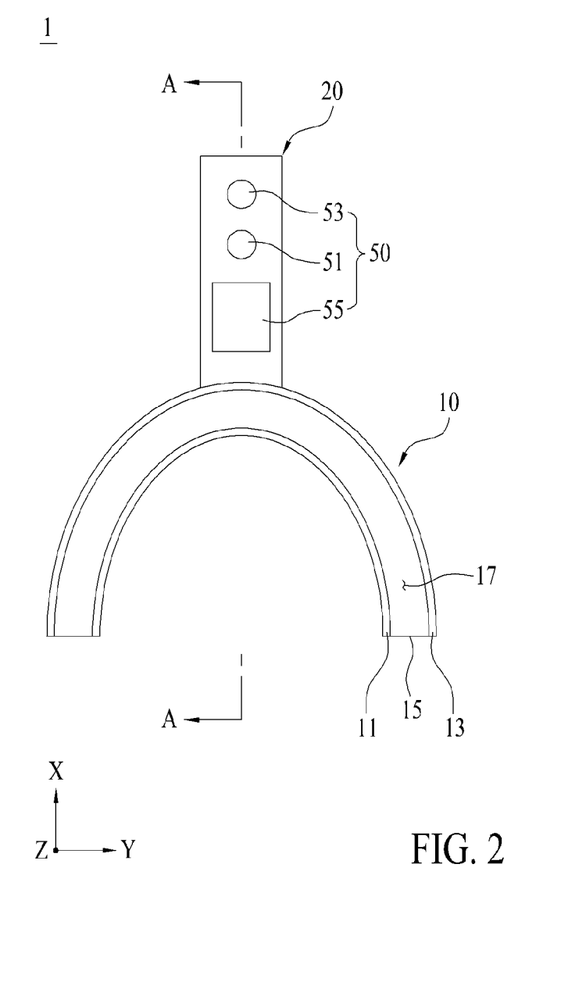
FIG. 2 is a plan view illustrating the tooth whitening device of FIG. 1.
Figure 3:
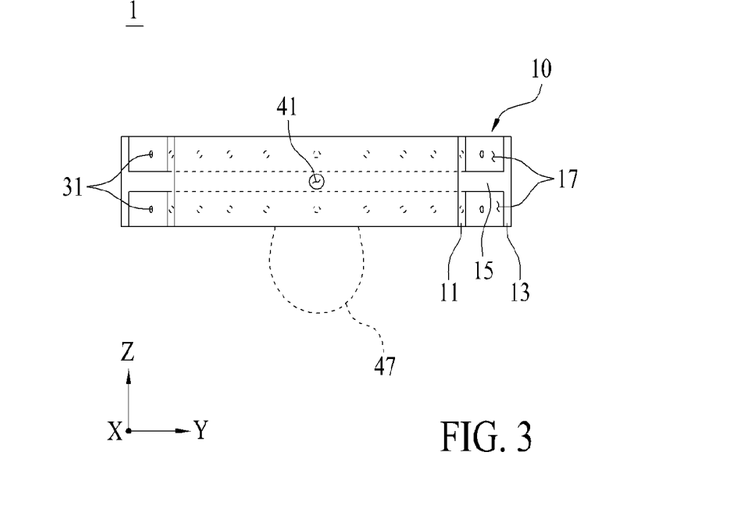
FIG. 3 is a front view illustrating the tooth whitening device of FIG. 1.
Figure 4:
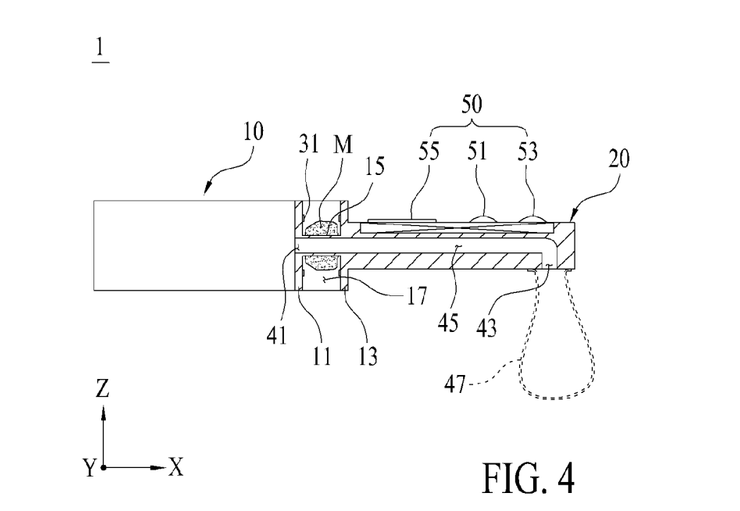
FIG. 4 is a cross-sectional view illustrating the tooth whitening device of FIG. 2 taken along line A-A'.

FIG. 1 is a perspective view illustrating a tooth whitening device according to one embodiment of the present invention, FIG. 2 is a plan view illustrating the tooth whitening device of FIG. 1, FIG. 3 is a front view illustrating the tooth whitening device of FIG. 1, and FIG. 4 is a cross-sectional view illustrating the tooth whitening device of FIG. 2 taken along line A-A'.

Referring to FIGS. 1 to 4, a tooth whitening device 1 includes a main frame 10, a support member 20, a light emitting member 30, a fluid storage member 40, and a control member 50.

Here, a direction in which the main frame 10 and the support member 20 are sequentially arranged is referred to as a first direction X. When viewed from above, a direction perpendicular to the first direction X is referred to as a second direction Y. A direction perpendicular to both the first direction X and the second direction Y is referred to as a third direction Z.

The main frame 10 provides a space which holds a tooth part during tooth whitening treatment. A whitening groove 17 which will be described below is formed in the main frame 10. The main frame 10 may be provided in a horseshoe shape. As an example, the main frame 10 may have a horseshoe shape opened opposite to a direction in which the support member 20 is located in the first direction X. The main frame 10 may be formed of a plastic material. As an example, the main frame 10 may include a transparent plastic material. On the other hand, the main frame 10 may be formed of a silicone or a transparent plastic material coated with a silicone. The main frame 10 is formed of the above materials such that discomfort, such as irritation to gums and the like, may be minimized.

The main frame 10 includes an inner frame 11, an outer frame 13, and a bottom frame 15.

The inner frame 11 may be located in front of the support member 20 in the first direction X. Here, a front of the first direction X is defined as a direction in which the main frame 10 is located on the basis of the support member 20, and a direction opposite thereto is defined as a rear of the first direction X.

The inner frame 11 may have a horseshoe shape. As an example, the inner frame 11 may have a horseshoe shape opened toward the front of the first direction X. The inner frame 11 may be formed of a plastic material. The inner frame 11 may be formed of a transparent material. On the other hand, the inner frame 11 may be formed of a silicone or a transparent plastic material coated with a silicone. The inner frame 11 may be formed in a plate shape having a certain thickness and a horseshoe shape.

The outer frame 13 may be located to the rear of the inner frame 11 in the first direction X. The outer frame 13 may have the same shape as that of the inner frame 11. The outer frame 13 may have a greater size than that of the inner frame 11. The outer frame 13 may have a horseshoe shape. As an example, the outer frame 13 may have a horseshoe shape opened toward the front of the first direction X. The outer frame 13 may be formed of a plastic material. The outer frame 13 may be formed of a transparent material. On the other hand, the outer frame 13 may be formed of a silicone or a transparent plastic material coated with a silicone. The outer frame 13 may be formed in a plate shape having a certain thickness and a horseshoe shape.

The bottom frame 15 may be located between the outer frame 13 and the inner frame 11.

One end of the bottom frame 15 may be coupled with the inner frame 11, and the other end thereof may be coupled with the outer frame 13. The bottom frame 15 may be coupled with a center part of the inner frame 11 on the basis of a length thereof in the second direction Y. The bottom frame 15 may be coupled with a center of the outer frame 13 on the basis of a length thereof in the second direction Y. The bottom frame 15 has a plate shape and a horseshoe shape.

The bottom frame 15 may be formed of a plastic material. The bottom frame 15 may be formed of a transparent material. On the other hand, the bottom frame 15 may be formed of a silicone or a transparent plastic material coated with a silicone.

A surface of the main frame 10 located to the rear of the inner frame 11 in the first direction X, a surface of the outer frame 13 located in front of the first direction X, and a top surface and a bottom surface of the bottom frame 15 in the third direction Z may be combined with each other to form two tooth whitening grooves 17.

The tooth whitening grooves 17 may hold teeth. A tooth whitening agent M may be applied to the tooth whitening grooves 17. As an example, the tooth whitening agent M is a gel type having viscosity and may be attached to the inner frame 11, the outer frame 13, and the bottom frame 15.

The tooth whitening grooves 17 may hold upper teeth and lower teeth when a user receives tooth whitening treatment. The tooth whitening groove 17 may have a horseshoe shape which is similar to a teeth-arranged shape.

Since the tooth whitening agent M is applied to the tooth whitening grooves 17 in advance, it is unnecessary to apply an additional tooth whitening agent to the tooth whitening device 1 when performing tooth whitening treatment. Also, since the gel type tooth whitening agent M may be applied so as to be attached to a periphery of the tooth whitening grooves 17, it is possible to prevent the tooth whitening agent M from flowing outward or being detached to lapse while the tooth whitening device 1 is being moved.

The support member 20 may be coupled with the main frame 10. The support member 20 may be located to the rear of the main frame 10 in the first direction X. The support member 20 may be coupled with a surface of the outer frame 13 located to the rear of the first direction X. The support member 20 may function as a handle.

The light emitting member 30 may emit light toward teeth during tooth whitening treatment. A plurality of such light emitting members 30 may be provided inside the main frame 10. As an example, the light emitting members 30 may be provided as a plurality of lamps 31. The plurality of lamps 31 may be located to be spaced at a certain distance from each other on a surface of the outer frame 13 located in front of the first direction X. As an example, the lamps 31 may be light emitting diode (LED) lamps. Otherwise, any well-known lamps that are usable for tooth whitening may be applied without limitation.

The fluid storage member 40 may store a fluid such as saliva and the like which flows from an inside of the mouth during tooth whitening. At least a part of the fluid storage member 40 may be located to pass through inside the main frame 10 and the support member 20.

The fluid storage member 40 includes a fluid inlet 41, a fluid outlet 43, a fluid channel 45, and a fluid storage portion 47.

The fluid inlet 41 may be located in the main frame 10. As an example, the fluid inlet 41 may be located in a surface of the inner frame 11 located in front of the first direction X. The fluid inlet 41 may be located in a surface of the inner frame 11 which is opposite to a side surface of the bottom frame 15. Specifically, as shown in FIG. 4, the fluid inlet 41 may penetrate the inner frame 11, inside of the bottom frame 15 and the outer frame 13. Saliva and the like may flow into the fluid inlet 41 during tooth whitening.

As illustrated in FIG. 4, the fluid channel 45 is formed inside of the support member 20. The fluid outlet 43 is an exit through which a fluid flowing into the fluid inlet 41 and flowing through the fluid channel 45 is discharged. The fluid outlet 43 may be located in one surface of the support member 20. As an example, the fluid outlet 43 may be located in a lower surface of the support member 20 in the third direction Z.

One end of the fluid channel 45 may be connected to the fluid inlet 41, and the other end thereof may be connected to the fluid outlet 43. A channel is formed passing through the inner frame 11, inside of the bottom frame 15, and the outer frame 13 (i.e., the fluid inlet 41 formed in the main frame 10), and leading to the fluid channel 41 formed inside the support member 20. A fluid such as saliva and the like in the mouth may flow through the fluid channel 45 during tooth whitening. The fluid channel 45 may be a linear channel.

The fluid storage portion 47 may store the fluid discharged from the fluid outlet 43. The fluid storage portion 47 may be coupled with the support member 20. The fluid storage portion 47 may be provided to be detachable from the support member 20. As an example, the fluid stored in the fluid storage portion 47 may be saliva. As an example, the fluid storage portion 47 may be formed in a plastic bag form.

The control member 50 may control whether the light emitting members 30 emit light or a light emission time of the light emitting members 30 during tooth whitening.

The control member 50 includes a manipulation portion 51, a timer portion 53, and a display portion 55.

The manipulation portion 51 may control whether the light emitting members 30 emit light. As an example, the manipulation portion 51 may be located on the support member 20. The manipulation portion 51 may be provided with a button. As an example, during tooth whitening, light emission of the light emitting members 30 may be started by pressing the button of the manipulation portion 51. The light emitting members 30 may be turned on by pushing the button of the manipulation portion 51 for a preset time. As an example, the preset time may be three seconds or more.

The manipulation portion 51 may have a device capable of emitting light to continuously emit light while the light emitting members 30 emit light. The manipulation portion 51 may not emit light when the light emitting members 30 are not emitting light.

The manipulation portion 51 may be provided with an additional power supply portion (not shown). The power supply portion may provide power for manipulation.

An example of an operation of the manipulation portion 51 will be described. An operation button is present in the manipulation portion 51. When the operation button is pushed, light of the button is turned on while simultaneously a notification sound is played such that the operation may be easily recognized. Also, an additional timer (not shown) is installed such that the operation is finished when a certain time passes. Here, the light of the operation button of the manipulation portion 51 is turned off and a completion notification sound is played such that the operation being finished may be easily recognized.

The timer portion 53 may control a light emission time of the light emitting members 30. The timer portion 53 may be located on the support member 20. The timer portion 53 may be provided in a button form. Whenever the timer portion 53 is pushed once, a certain length of light emission time may be provided. As an example, when a light emission time of five minutes is provided whenever the timer portion 53 is pushed once, the user may adjust the light emission time of the light emitting member 30 by manipulating the timer portion 53 as necessary.

The display portion 55 may be located on the support member 20. The display portion 55 may display a timer time of the timer portion 53, whether the light emitting members 30 emit light, and other pieces of information.

Although the control member 50 including the manipulation portion 51, the timer portion 53, and the display portion 55 has been described as an example above, unlike the above, the display portion 55 may not be provided. Also, although it has been described as an example that the manipulation portion 51 and the timer portion 53 are separately provided, one button may perform a function of the manipulation portion 51 and a function of the timer portion 53 at the same time.

Hereinafter, a process of performing tooth whitening treatment using the tooth whitening device 1 of the present invention will be described.

FIGS. 5 to 9 are views schematically illustrating the process of performing tooth whitening treatment using the tooth whitening device 1 according to one embodiment of the present invention.

Figure 5:
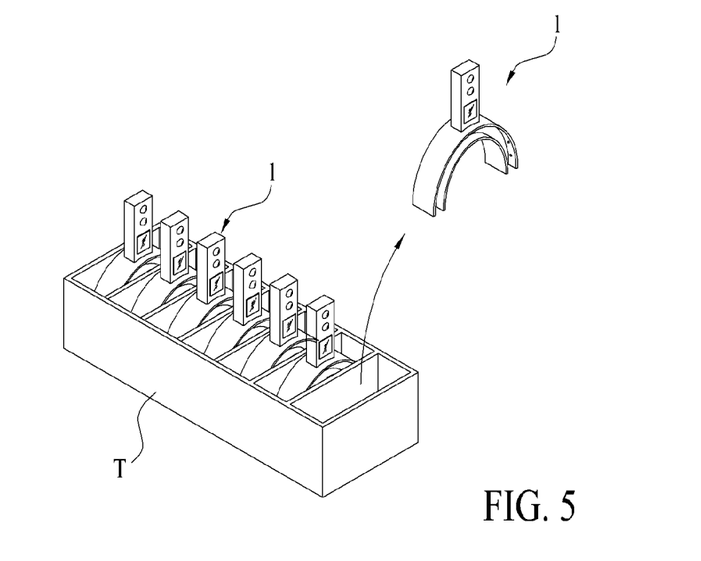
FIGS. 5 to 9 are views schematically illustrating a process of performing tooth whitening treatment using the tooth whitening device according to one embodiment of the present invention.
Figure 6:
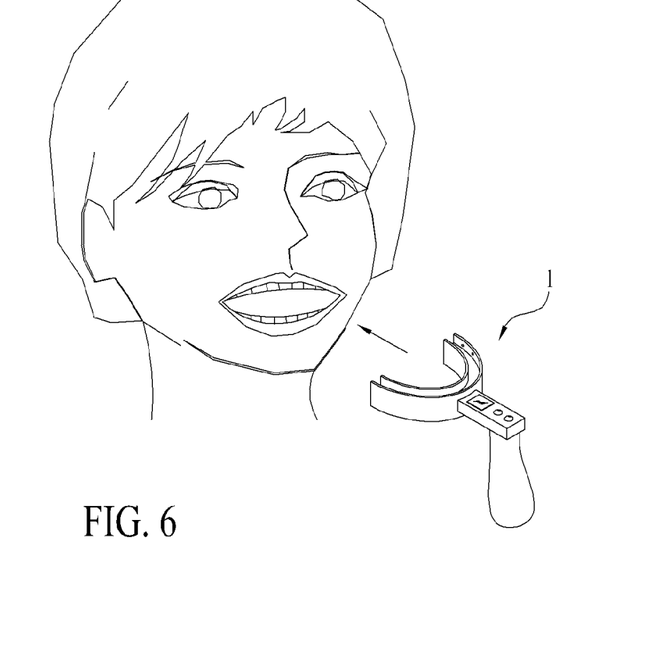
Figure 7:
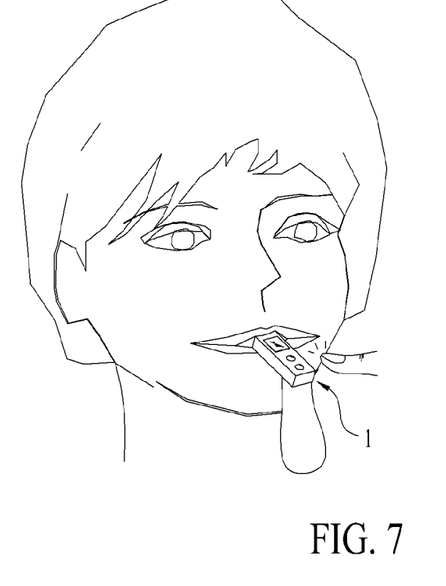
Figure 8:
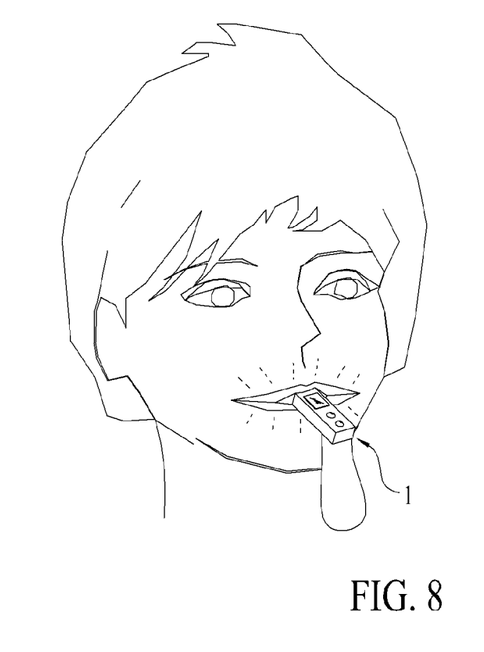
Figure 9:
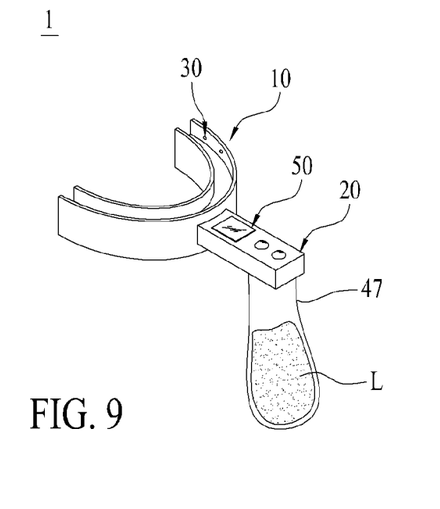

Referring to FIGS. 5 to 9, a plurality of such tooth whitening devices 1 of the present invention may be provided while being mounted as a set in one cartridge T. As an example, as shown in FIG. 5, the plurality of tooth whitening devices 1 may be provided in one cartridge.

During the tooth whitening treatment, the user may take out and use the tooth whitening device 1 from the cartridge T.

The user may take out the tooth whitening device 1 and insert teeth into the tooth whitening grooves 17 such that the teeth are held by the tooth whitening grooves 17. Afterwards, the user may start tooth whitening treatment and control a tooth whitening time using the manipulation portion 51 or the timer portion 53 of the control member 50.

During the toot whitening treatment, the tooth whitening agent M applied to the tooth whitening grooves 17 in advance may be applied to a tooth part. Afterwards, the tooth whitening treatment may be performed through light emission of the light emitting member 30. Saliva or other liquids generated in the mouth during the tooth whitening treatment are disposed in the fluid storage portion 47 of the tooth whitening device 1. In detail, saliva and the like may sequentially flow through the fluid inlet 41, the fluid channel 45, and the fluid outlet 43 and then be disposed in the fluid storage portion 47.

When the tooth whitening treatment is finished, the user stops light emission of the light emitting members 30 using the control member 50 and takes the tooth whitening device 1 out of the mouth. Afterwards, the user may separate the fluid storage portion 47 from the support member 20 and dump a fluid.

As described above, according to one embodiment of the present invention, tooth whitening treatment may be easily performed using the tooth whitening device 1 of the present invention in ordinary environments such as a home or a domestic environment. Also, since the tooth whitening device 1 of the present invention is manufactured at a low cost, users may purchase the tooth whitening device 1 at a low cost.

Also, according to one embodiment of the present invention, the fluid storage member 40 is provided to prevent saliva and the like generated in a mouth during tooth whitening treatment from flowing outward such that tooth whitening may be performed while a periphery of the mouth may be maintained to be clean.

According to one embodiment of the present invention, since it is possible to prevent a fluid such as saliva and the like in the mouth from being mixed with a tooth whitening agent and reducing a treatment effect or from flowing outward from a mouth during tooth whitening treatment and to store the tooth whitening agent in a fluid storage portion, tooth whitening treatment may be easily performed.

Also, since a power supply portion is included in a manipulation portion, tooth whitening treatment may be easily performed without the inconvenience of additionally connecting a power supply or inserting a battery.

Also, a tooth whitening device according to the present invention may be disposable and may be sanitarily and simply used.

The above detailed description exemplifies the present invention. Also, the exemplary embodiments of the present invention have been described above, and the present invention may be applied in a variety different combinations, changes, and environments. That is, changes or modifications may be made without departing from the scope of the concept of the present invention, the scope and/or skill in the art or scope of knowledge equivalent to the disclosed content. The above-described embodiments are merely used for describing an exemplary state for implementing the technical concept of the present invention, and a variety of modifications necessary for detailed application fields and use of the present invention may be made. Accordingly, there is no intention to limit the above detailed description of the present invention to the disclosed embodiments. Also, it should be construed that the attached claims include other embodiments.

The invention claimed is:

1. A disposable tooth whitening device consisting of:
 a main frame provided in a horseshoe shape and comprising tooth whitening grooves capable of holding teeth;
 a support member coupled with the main frame;
 a plurality of light emitting members installed in the main frame and configured to emit light during tooth whitening;
 a fluid storage member located to pass through the main frame and an inside of the support member and configured to pass saliva flowing from an inside of a mouth during the tooth whitening; and
 a control member configured to control a light emission time of the light emitting members and whether the light emitting members operate,
 wherein the main frame comprises:
  an inner frame provided in a horseshoe shape;
  an outer frame provided in a horseshoe shape and located to be spaced apart from the inner frame; and
  a bottom frame coupled with the inner frame and the outer frame and located between the inner frame and the outer frame,
 wherein the plurality of light emitting members are installed only on an inner wall of the outer frame surrounding the tooth whitening grooves,
 wherein the tooth whitening grooves are provided to be surrounded by the inner frame, the outer frame, and the bottom frame,
 wherein a gel type tooth whitening agent is pre-applied to the tooth whitening grooves, the tooth whitening agent is attached to the inner frame, the outer frame, and the bottom frame,
 wherein the fluid storage member comprises:
  a fluid inlet formed in the main frame, the fluid inlet being formed to penetrate the inner frame, inside of the bottom frame and the outer frame;
  a fluid outlet formed on one side surface of the support member; and
  a fluid channel located inside the support member and having one end connected to the fluid inlet and the other end connected to the fluid outlet to move a fluid flowing through the fluid inlet toward the fluid outlet, the fluid channel and the fluid inlet forming a channel passing through an inside of the main frame and an inside of the support member
 wherein a fluid storage portion is detachably coupled with the support member and configured to store the fluid discharged from the fluid outlet.

2. The tooth whitening device of claim 1, wherein the inner frame, the outer frame, and the bottom frame are formed of a transparent plastic material.

3. The tooth whitening device of claim 1, wherein the light emitting members comprise a plurality of lamps, and the plurality of lamps are spaced at certain intervals apart from each other on the inner wall of the main frame surrounding the tooth whitening grooves.

4. The tooth whitening device of claim 1, wherein the control member comprises:
 a manipulation portion configured to control whether the light emitting members emit light; and
 a timer portion configured to control the light emission time of the light emitting members.

5. The tooth whitening device of claim 4, wherein the manipulation portion comprises a manipulation lamp configured to continuously emit light outward while the light emitting members emit light.

* * * * *